United States Patent [19]
Jumppanen et al.

[11] Patent Number: 6,140,498
[45] Date of Patent: Oct. 31, 2000

[54] PROCESS FOR THE CONTINUOUS PRODUCTION OF HIGH PURITY L-RIBOSE

[75] Inventors: Juho Jumppanen, Espoo; Juha Nurmi, Kirkkonummi; Ossi Pastinen, Kantvik, all of Finland

[73] Assignee: Xyrofin Oy, Helsinki, Finland

[21] Appl. No.: 09/193,466

[22] Filed: Nov. 17, 1998

[51] Int. Cl.⁷ ...................................................... C07H 1/06
[52] U.S. Cl. .............................................. 536/125; 536/1
[58] Field of Search ...................................... 536/125, 1.1

[56] References Cited

U.S. PATENT DOCUMENTS

| | | | |
|---|---|---|---|
| 4,029,878 | 6/1977 | Kruse | 536/1.11 |
| 4,355,158 | 10/1982 | Wolf et al. | 536/1 |
| 4,602,086 | 7/1986 | Hiroshi et al. | 536/125 |
| 4,718,405 | 1/1988 | Firth et al. | 127/46.1 |
| 4,778,531 | 10/1988 | Dobler et al. | 127/46.1 |
| 4,815,445 | 3/1989 | Swedo et al. | 127/46.1 |
| 5,015,296 | 5/1991 | Dobler et al. | 127/42 |

FOREIGN PATENT DOCUMENTS

| | | |
|---|---|---|
| 149472 | 7/1973 | Czechoslovakia . |
| 275890 | 3/1992 | Czechoslovakia . |
| 0 252 361 A2 | 1/1988 | European Pat. Off. . |
| 0 288 847 A2 | 4/1988 | European Pat. Off. . |
| 60081196 | 5/1985 | Japan . |
| 11012294 | 1/1999 | Japan . |
| 89/07602 | 8/1989 | WIPO . |
| WO 89/07602 | 8/1989 | WIPO . |

OTHER PUBLICATIONS

Bilik et al., "Reactions of saccharides catalyzed by molybdenate ions. VII. Preparation of L–ribose, D–and L–lyxose", Chem. Zvesti, vol. 27(4): 547–550, 1973.
Fluka Chemika–Biochemika Product Catalog, p. 444, 1995.
Carbohydrates. edited by John F. Kennedy, publ. by Chapman Hall, p. 444, 1987.
Japanese Abstract No. 55076894. Jul. 10, 1980.
Japanese Abstract No. 57054197. Mar. 31, 1982.
V. Bilik, "Reactions of Saccharides Catalyzed by Molybdate Ions. II.* Epimerization of D–Glucose and D–Mannose," Chem. Zvesti, No. 26, pp. 183–186 (1972).
V. Bilik, "Reactions of Saccharides Catalyzed by Molybdate Ions. IV.* Epimerization of Aldopentoses," Chem. Zvesti, No. 26, pp. 372–375 (1975).
Y. Abe, et al., "Epimerization of Aldoses Catalyzed by Dioxobis(2,4–pentanedionato–0,0')–Molybdenum (VI). An Improved Procedure for C–2 Epimer Preparation," Chem. Pharm. Bull., vol. 28, pp. 1324–1326 (1980).

*Primary Examiner*—Howard C. Lee
*Attorney, Agent, or Firm*—Scully, Scott, Murphy & Presser

[57] ABSTRACT

A process of preparing a L-ribose fraction having greater than 97% purity starting from an aqueous solution of L-arabinose is provided by utilizing an epimerization reaction conducted in the presence of a Mo compound and eluting the product formed by said epimerization reaction through a separation zone containing a strong acid cation exchange resin. A process of crystallized said L-ribose fraction under conditions effective to form monohydrate L-ribose crystals is also disclosed.

67 Claims, No Drawings

PROCESS FOR THE CONTINUOUS PRODUCTION OF HIGH PURITY L-RIBOSE

FIELD OF THE INVENTION

The present invention relates to the manufacturing and production of L-ribose crystals from a solution of L-arabinose. Specifically, a process of preparing a L-ribose fraction having a purity greater than 90% using L-arabinose as a starting material is provided. The process of preparing the high purity L-ribose fraction comprises catalytically converting L-arabinose to L-ribose in the presence of a Mo compound under conditions wherein equilibrium is not obtained and thereafter separating the L-ribose from the catalytic solution using a selective ion exchange resin which has a high selectivity capacity for L-ribose.

A process of crystallizing and recovering high purity L-ribose crystals (>95% purity) that are essentially anhydrous (less than 0.5% $H_2O$) from said L-ribose fraction is also provided herein. It is noted that the crystallization process of the present invention forms monohydrate L-ribose crystals which can be converted to the anhydrous form.

These respective processes are integrated into a unitary continuous process of preparing L-ribose crystals having a purity of greater than 95%. The L-ribose crystals produced by the processes of the present invention have substantially no impurities and little or no detectable amounts of L-sugars or other impurities besides L-ribose present therein. This represents a significant advancement over prior art processes wherein chiral impurities and other L-sugars are oftentimes present in L-ribose crystals.

BACKGROUND OF THE INVENTION

In the pharmaceutical industry, high purity reactants are generally required as starting materials for producing drugs for treating individuals inflicted with a specific disease. Typically, it is required that the high purity reactants have little or no detectable amounts of impurities present therein since impurities, even if present in minor amounts, can carry over to the final product being produced. Thus, the presence of even trace amounts of impurities in the reactants is undesirable since they may adversely effect the final product or, in extreme cases, cause side-reactions to the patient to whom the drug is being administered.

One area wherein highly pure chiral reactants are sought is in developing new and improved drugs containing a benzimidazole riboside compound. This compound is currently being used for treating various human disorders such as HIV. In order to produce benzimidazole riboside compounds of high quality and quantity, highly pure L-ribose crystals are required as a reactant.

Although the prior art contains myriads of processes of producing ribose (D- or L-form), those prior art processes, including those described hereinbelow, do not form L-ribose crystals of sufficient purity which allows for the production of high purity benzimidazole riboside compounds.

In the prior art, D-ribose has been generally prepared industrially by a process in which D-glucose is oxidized with oxygen in an aqueous alkali solution to form D-arabonic acid which is isolated in the form of a metal salt, e.g., the mercurial zinc salt, and epimerized and lactonized to give D-ribonolactone; the latter is thereafter reduced with sodium amalgam to D-ribose. Heating D-arabonic acid in an aqueous alkali solution gives a mixture in which the equilibrium ratio of D-arabonic acid to D-ribonic acid is 70:30. In this prior art procedure, it is impossible to obtain a mixture containing more than 30% of D-ribonic acid. Moreover, large amounts of mercury, which present difficulties in the process, are required to form the amalgam.

Bilik et al. reported that various saccharides could be epimerized in an aqueous solution in the presence of a molybdic acid catalyst, including the epimerization of L-arabinose to L-ribose (see, for instance, Czechoslovak Pat. No. 149,472; Chemical Abstracts 81, 78 189 K).

On the basis of this knowledge, a process was developed in which D-gluconic acid was oxidized to D-arabinose instead of D-arabonic acid. Hypochlorite was used as the oxidizing agent. D-arabinose was then epimerized in an aqueous solution in the presence of a molybdenum catalyst to give D-ribose (cf. Japanese Preliminary Published Application No. 164,699 1980 and European Pat. No. 20,959 and U.S. Pat. No. 4,355,158). This process achieves an epimerization ratio (proportion of ribose in an equilibrium mixture) of only about 25%. Nevertheless, this process is superior to the one described above, since no mercury is used and fewer steps are required. In one version of the process, a major part of the arabinose is isolated in crystalline form and recycled to the epimerization reaction. To facilitate separation of the molybdic acid from the epimerization solution, the use of a molybdic acid-carrying ion exchanger resin instead of molybdic acid (cf. Japanese Patent Publication No. 40 700/1981) or the use of a molybdic acid-carrying ion exchanger fiber (cf. Japanese Preliminary Published Application No. 76 894/1980) has been described. The epimerization ratio of D-arabinose to D-ribose is 69.4:30.6. Japanese Preliminary Published Application No. 54 197/1982 discloses an epimerization ratio of 27.2% of D-ribose.

It is also known that, by heating L-arabinose in dimethylformamide in the presence of dioxobis-(2,4-pentadionate-0,0')-molybdenum (VI), 36% of the L-arabinose is epimerized to L-ribose (cf. Abe et al., Chemical and Pharmaceutical Bulletin, 28 (1980), 1324).

Further improvement in the ribose selectivity is achieved by adding boron compounds in a 2 to 3-fold molar amount to the epimerization mixture (cf. JP-OS No. 1,890,976/83, JP-OS No. 223,187/83 and German Laid-Open Application No. DOS 3,437,571). This gives an epimerization equilibrium of about 60% in aqueous solutions and up to 94% in nonaqueous solutions. The disadvantage of this process is that the boric acid cannot be separated to an extent acceptable for vitamin $B_2$ preparation without ribose and arabinose also being removed, i.e. the yield of total sugars decreases sharply with each measure to separate the boric acid. Moreover, the unconverted arabinose in the boric acid-containing solution cannot be separated from ribose and reused.

Other references which disclose alternative methods for producing D-ribose from D-arabinose are described in U.S. Pat. Nos. 4,778,531 and 5,015,296. In the '531 patent, the epimerization of D-arabinose to D-ribose is carried out in an aqueous solution in the presence of a Mo(IV) compound and a metal salt of the formula $MeX_2$, wherein Me is Mg, Ca, Sr, Ba or Zn and X is Cl or Br. In regard to the '296 patent, the epimerization reaction is carried out in the presence of a basic cation exchanger that is charged with a Mo(IV) compound.

Despite the current state of the art, there is a continued need to develop a new and improved process which can efficiently and continuously produce high purity L-ribose crystals starting from a solution of L-arabinose. This is especially so in the pharmaceutical industry wherein highly pure L-ribose crystals are needed as a starting material for producing, for example, antiviral drugs. In particular, highly pure L-ribose crystals, having no chiral impurities, are being sought as a starting material for producing benzimidazole riboside compounds. Such benzimidazole riboside compounds have recently been reported as an effective inhibitor of cytomegalovirus DNA synthesis without exhibiting any significant side effects in patients treated with the benzimidazole riboside compound. As is known to those skilled in HIV research, the cytomegalovirus causes blindness in HIV effected patients.

SUMMARY OF THE INVENTION

One object of the present invention is to provide a process of preparing a highly pure L-ribose fraction from a solution of L-arabinose.

Another object of the present invention is to provide a process of producing a highly pure L-ribose fraction from a solution of L-arabinose wherein the conversion efficiency is maximized and the amount of side products is minimized.

A further object of the present invention is to provide a separation process which has a high affinity for L-ribose as compared to other L-sugars.

A yet further object of the present invention is to provide a process whereby a high purity L-ribose fraction can be crystallized into highly pure L-ribose crystals that have little or essentially no impurities therein.

These and other objects and advantages are achieved by the present invention wherein an improved process of preparing an L-ribose fraction having a purity greater than 90% is achieved by controlling the degree of conversion of L-arabinose to L-ribose and by utilizing a strong acid cation exchanger in $Pb^{+2}$-form to separate L-ribose from other materials, e.g. L-sugars, present in the epimerization reaction. The conversion reaction is carried out in the absence of metal salts and under conditions whereby equilibrium is not achieved.

Specifically, in one aspect of the present invention, highly pure L-ribose crystals are produced and recovered by a process comprising the steps of:

(a) heating a solution of L-arabinose in a stirred reaction zone and in the presence of from about 0.05 to about 5 mol %, based on the total amount of L-arabinose present in said solution, of a Mo compound under conditions whereby 10–35%, an amount of said L-arabinose less than reaction equilibrium, is converted to L-ribose;

(b) separating said L-ribose from the heated solution of step (a) under conditions to provide at least one fraction containing L-ribose having a purity of greater than 90%, wherein selected other fractions are transferred back to said stirred reaction zone or into a chromatographic separation;

(c) crystallizing said L-ribose fraction under conditions effective to form monohydrate L-ribose crystals; and (d) recovering highly pure L-ribose crystals.

In another aspect of the present invention, a L-ribose fraction having a purity greater than 90% is provided. This fraction is produced in the present invention by:

(a) heating a solution comprising L-arabinose in a stirred reaction zone and in the presence of from about 0.05 to about 5 mol %, based on the total amount of L-arabinose in said solution, of a molybdenum compound under conditions whereby 10–35% of said L-arabinose is converted to L-ribose;

(b) transferring said reaction solution formed in step (a) to a separation zone, wherein said separation zone comprises a strong acid cation exchange resin in lead form; and (c) eluting said reaction solution through said separation zone under conditions to provide at least one fraction containing L-ribose having a purity greater than 90%, wherein other selected fractions provided in said eluting step are transferred back to said stirred reaction zone or into another chromatographic separation zone.

In yet another aspect of the present invention, a process of preparing L-ribose crystals is provided. Specifically, this aspect of the present invention comprises:

(a) heating, in the absence of a metal halide, a solution comprising L-arabinose in a stirred reaction zone and in the presence of from about 0.1 to about 1 mol %, based on the total amount of L-arabinose in said solution, of a molybdenum compound under conditions whereby 15–25% of said L-arabinose is converted to L-ribose;

(b) transferring said reaction solution formed in step (a) to a separation zone, wherein said separation zone comprises a strong cation exchanger in lead form;

(c) eluting said reaction solution through said separation zone under conditions to provide at least one fraction containing L-ribose having a purity greater than 90%, wherein other selected fractions provided in said eluting step are transferred back to said stirred reaction zone or into chromatographic separation;

(d) evaporating said L-ribose fraction under conditions to form a mixture having a dry solid content of from about 85% or above;

(e) cooling said mixture containing said L-ribose below about 40° C. and effecting monohydrate L-ribose crystal growth at said temperature by seeding said cooled mixture with anhydrous ribose crystals; and (f) recovering said L-ribose crystals.

In a further aspect of the present invention, a process of crystallizing and recovering L-ribose crystals from a chromatographic separated L-ribose fraction is provided. Specifically, this aspect of the present invention comprises the steps of:

(a) providing a L-ribose rich aqueous solution having a L-ribose content greater than 90%;

(b) evaporating said L-ribose solution under conditions effective to form a mixture having a dry solid content of from about 85% or above;

(c) cooling said mixture containing said L-ribose below about 40° C. and effecting monohydrate L-ribose crystal growth at said temperature by seeding said cooled mixture with anhydrous ribose crystals; and (d) recovering L-ribose crystals.

DETAILED DESCRIPTION OF THE INVENTION

As stated above, one aspect of the present invention relates to a continuous process of preparing a L-ribose fraction having a purity of greater than 90% starting from a solution which contains L-arabinose. More preferably, the purity of L-ribose fraction produced by the process of the present invention is from about 95 to about 99%.

In accordance with this aspect of the present invention, L-ribose is produced by catalytically converting a solution of L-arabinose into L-ribose. This catalytic conversion is referred to herein as an epimerization reaction. Without wishing to be bound by any theory, it is postulated herein that the conversion of L-arabinose to L-ribose involves the formation of a ribulose intermediate. This postulate appears to be confirmed by the fact that the reaction solution, after heating, contains a fraction of ribulose which, prior to the present invention, was difficult to separate from the other fractions produced. It is emphasized that by employing the following reaction, separation and crystallization steps, the final L-ribose crystals contain less than 0.03% ribulose which is well below the GC/MS detection limit for that compound.

The L-arabinose solution employed in the present invention comprises from about 1 to about 60% L-arabinose which is present in a solvent that is capable of dissolving said L-arabinose. More preferably, the starting solution of L-arabinose comprises from about 10 to about 15% L-arabinose in a solvent that is capable of dissolving said L-arabinose. It is noted that the L-arabinose solution may also contain other L-sugars and/or impurities besides L-arabinose. The L-arabinose employed in the present invention can be recovered from arabinose containing hemicellulose hydrolyzate as hardwood prehydrolyzate, hardwood spent liquor or sugar beet pulp hydrolyzate.

Suitable solvents which can be employed in the present invention to dissolve the L-arabinose include, but are not limited to: water, alcohols such as methanol or ethanol, or ethers such as ethylene glycol or ethylene glycol ether. Mixtures of these solvents are also contemplated herein. In a highly preferred embodiment of the present invention, the solvent employed for dissolving the L-arabinose is water.

Specifically, the epimerization reaction of the present invention is carried out by heating a L-arabinose solution in the presence of a Mo compound under conditions wherein about 10 to about 35% of said L-arabinose is converted to L-ribose. More preferably, about 15 to about 25% L-arabinose is converted to L-ribose using the epimerization reaction conditions described hereinbelow. This heating step is carried out in a continuous stirred reaction zone including, but not limited to, a continuous stirred tank reactor.

As stated above, the conditions employed in the heating step are such that illustratively from about 10 to about 35% of said L-arabinose is converted to L-ribose. Thus, unlike prior art processes, the epimerization reaction conditions employed in the present invention are such that full equilibrium of the reaction is not achieved. In practice, under the selected operating conditions of the present invention, the degree of conversion is controlled so as to secure the maximum product conversion (yield) without development of undesired color bodies. Moreover, the epimerization reaction of the present invention is not carried out in the presence of a metal halide such as is described and required in U.S. Pat. No. 4,778,531.

The amount of Mo compound employed in the present invention to achieve the above conversion is from about 0.05 to about 5 mol %. More preferably, the conversion of L-arabinose to L-ribose is carried out in the presence of from about 0.1 to about 1 mol %, based on the total amount of said L-arabinose, of a Mo compound. Most preferably, the amount of Mo compound employed in the conversion step is from about 0.3 to about 0.5 mol %.

Suitable Mo compounds that can be employed in the present invention include compounds such as, but not limited to: $MoO_3$, $H_2MoO_4$, $(NH_4)_2MoO_4$ and other salts of $MoO^{2-}_4$. Mixtures of these Mo compounds are also contemplated herein. Of the foregoing Mo compounds, it is highly preferred that the Mo compound is $MoO_3$.

The heating step of the present invention, which accomplishes the desired conversion of L-arabinose to L-ribose, is carried out at a temperature of from about 60° to about 110° C. for a time period of from about 0.1 to about 24 hours. More preferably, the heating step is carried out at a temperature of from about 92° to about 98° C. for a time period of from about 2 to about 3 hours.

Another aspect of the heating step of the present invention is that the reactant solution containing said L-arabinose solution and Mo compound requires no adjustment of the pH which is typically required in the prior art to maintain equilibrium. Since equilibrium of the epimerization reaction is not desired in the present Invention, the pH of the reactant solution does not need to be adjusted.

In using the above reaction conditions, an essentially clear reaction solution comprising a mixture of L-arabinose, L-ribose, ribulose, xylose, galactose, lyxose and Mo compound is obtained. Other L-sugars besides those mentioned herein may also be present. By "essentially clear" it is meant that the reaction solution, after heating, contains essentially no colored bodies which would prevent light from being transmitted through the solution.

This is unlike prior art processes which produce solutions that are generally colored. Thus, a required consequence of the prior art, which is optional and generally unnecessary in the present invention, is that the colored solution be decolored prior to conducting chromatographic separation.

The thus obtained reaction solution comprising the mixture of L-arabinose, L-ribose, ribulose, Mo compound and other L-sugars is then transferred from the stirred reaction zone into a separation zone. Although not required by the present invention, the reaction solution may optionally be subjected to conventional ion exchange chromatography wherein any excess Mo used in the conversion step can be removed therefrom. When such a step is employed, any ion exchange resin which has a high affinity for Mo can be used. One such example of an ion exchange resin that can be employed in the present invention is DOW 66. DOW 66 is a spherical ion exchange resin which has a backbone of styrene divinylbenzene and it is macroporous. The active group in the resin is dimethyl ammonium. The resin is cationic thus it binds anions from the solution. Because it contains tertiary amine groups, it is a weak anion exchange resin.

The reaction solution or, optionally ion exchanged solution, is then subjected to liquid chromatography so as to provide at least one fraction containing L-ribose having a purity of greater than 90%. It is noted that if other eluted fractions are obtained they can be either returned to the stirred reaction zone or be subjected to further chromatographic separation. Specifically, the high purity L-ribose fraction is separated from the reaction mixture by transferring the same to a separation zone containing an ion exchange resin and then eluting the same through said ion exchange resin under conditions to provide the L-ribose fraction having the desired purity.

Suitable ion exchange resins employed in the present invention are those which have a high capacity value, i.e. affinity, for L-ribose as compared with the other L-sugars. Typically, the ion exchange resin employed in the present invention is a strong acid cation exchange resin which preferably contains a polystyrene/divinylbenzene skeleton. More preferably, the ion exchange resin employed in the present invention is of the $Pb^{+2}$-form. A highly preferred $Pb^{+2}$-form ion exchange resin employed in the present invention is a sulphonated polystyrene resin which is crosslinked with from about 3 to about 16, more preferably 8–10, % divinylbenzene.

By employing the $Pb^{+2}$-form of the ion exchange resin, applicants have unexpectedly determined that the separation process is more selective than heretofore reported using $Ca^{+2}$, $La^{+2}$ or $Ba^{+2}$-exchangers. Specifically, applicants have determined that the selectivity value for separating ribose from ribulose using the $Pb^{+2}$-form of the exchanger (1.22) is higher than $Ca^{+2}$-exchangers (1.05), $La^{+2}$-exchangers (1.04) or $Ba^{+2}$-exchangers (1.14). This increased selectivity allows for combined ultra-high capacity selective and efficient separation of L-ribose from especially L-ribulose, usually the key impurity found in L-ribose. Selectivity values for separating ribose from arabinose with corresponding resins are: Pb 2.8; Ca 2.3; La 4.0 and Ba 1.6. The use of $Pb^{+2}$-form resin gives best results because selectivity for ribose with all other L-sugars present in the reaction mixture is good.

The separation zone employed in the present invention can be in the form of a batch column or in a simulated moving bed form. The reaction solution is allowed to flow through the separation zone at a flow rate of from about 0.2 to about 10 linear meters per hour at a temperature of from about 10° to about 90° C. More preferably, the reaction solution is eluted at a flow rate of from about 1 to about 3 linear meters per hour at a temperature of from about 50° to about 65° C.

The above described separation step provides at least one fraction having a purity greater than 90%. Typically such fraction contains from about 95 to about 99% L-ribose. Other major fractions separated from the process contain L-arabinose, ribulose, xylose, glucose, galactose and lyxose. In a typical separation process, the other eluted fractions contain from about 20 to about 90% L-arabinose, from about 0 to about 10% xylose, from about 0 to about 2% glucose, from about 0 to about 2% galactose, from about 0 to about 5% lyxose and from about 0 to about 5% ribulose. More preferably, the eluted fraction contains about 97 to about 98% L-ribose, about 0 to about 0.5% L-arabinose, about 0 to about 0.5% xylose, about 0 to about 2% ribulose and about 0 to about 0.5% lyxose. Other ranges are also possible depending on the separation conditions employed.

The highly pure L-ribose fraction obtained from the separation zone can then be subjected to crystallization and recovery as defined hereinbelow. Specifically, the high L-ribose fraction obtained above (purity 90% or greater) is evaporated under conditions to form a mixture that has a dry solid content of from about 85% or above. More preferably, evaporation is carried out until a dry solids content of from about 88 to about 92% is obtained. The evaporation step is carried out under vacuum at a temperature of from about 30° to about 70° C. and for a time period of from about 0.5 to about 15 hrs. More preferably, the evaporation is carried out at a temperature of from about 35° to about 55° C. and for a time period of from about 1 to about 5 hrs.

After evaporating the L-ribose fraction, the evaporated solution is then cooled below about 40° C., more preferably, below about 38° C., and crystallization is effected at said temperature by seeding the cooled evaporating solution with ribose crystals. It is noted that at higher temperatures ribose monohydrate crystals do not appear. This is because the solubility of the L-ribose crystals at higher temperatures is most likely greater than the water content of the crystals. In one embodiment of the crystallization process, cooling is continued until a temperature of from about 10° to about 30° C. is reached and then the solution is maintained at the temperature for a time period of from about 0 to about 100 hours More preferably, the solution is maintained at said temperature for a time period of from about 5 to about 10 hours. A yield of 45% or above, based on the dry solid content, of the crystals is typically obtained.

Generally, in the present invention, the cooling and crystallization is continued at a maximum rate of about 5 to about 0.2° C./hr. The total time for crystal formation is generally about 5 to about 100 hrs, and, more preferably, from about 10 to about 50 hrs. The ribose crystals used for seeding contain less than 5% water and Typically have a particle size of from about 5 to about 100 micrometers. In accordance with the present invention, from about 0.001 to about 1 wt % of seed crystals are added to the evaporated solution.

If the viscosity of the evaporated mixture is too thick for convenient handling or, if it becomes too thick during the crystallization process, a conventional viscosity reducing agent may be added. Suitable viscosity reducing agents that may be employed in the present invention include, but are not limited to: alcohols, hydrocarbons and other water miscible solvents. In a highly preferred embodiment, the viscosity reducing agent is an alcohol, with ethanol being the most preferred alcohol. When ethanol is employed, it is added during the cooling crystallization process at a temperature of below 35° C.

To effect crystal growth, the crystallization step is carried out in the presence of a stirring means such as a mechanical stirrer which is effective in forming needle-like L-ribose crystal having a particle size less than 500 micrometers. A preferred particle size of said L-ribose crystals obtained is from about 20 to about 100 micrometers. The product crystals formed by the present invention may exist in salt form or as hydrates, alcoholates and other like forms.

In accordance with the present invention, the desired crystal size is obtained using a stirrer which operates under high shear conditions, i.e. at temperature of from about 10° to about 40° C. and a mixing speed of from about 0.5 to about 50 rpm.

The thus produced L-ribose crystals are then separated and recovered from the mother-liquid; i.e., solution from which L-ribose crystals are crystallized, using conventional means well known to those skilled in the art. This includes centrifugation, washing, i.e. purifying, dehydration, filtration or a combination thereof. After these techniques are employed, drying is typically conducted at a temperature of from about 0° to about 40° C. for a time period of from about 0.5 to about 50 hours. More preferably, drying is carried out at a temperature of from about 10° to about 30° C. for a time period of from about 1 to about 10 hours.

In an optional; but highly preferred embodiment of the present invention, after the cooling step, the monohydrate L-ribose crystals are purified and partially dehydrated by washing the same at least once with a recrystallizing, i.e. dehydrating, solvent such as an alcohol or anhydrous ether. In a preferred embodiment of the present invention, ethanol is employed as the recrystallizing solvent. This recrystallizing, i.e. purifying and dehydrating step, provides highly pure anhydrous L-ribose crystals ($H_2O$ content of less than about 0.5%) of the desired size and purity. After recrystallization, the washed crystals are dried utilizing the drying conditions mentioned above.

The above-defined steps produce high purity L-ribose crystals (95% or above purity) that have little or no chiral impurities or other impurities such as Pb, Mo, ribulose, etc. Moreover, when the purification and partial dehydration steps are employed, the L-ribose crystals produced in accordance with the present invention have a low water content, less than 0.5%, and are characterized as being a free-flowing white powder of fine dimensions having a particle size of about 50–100 micrometers. Such a product is especially useful as a starting material in the production of benzimidazole riboside compounds that have recently shown promise in treating cytomegalovirus.

The mother-liquid from the crystallization step may be transferred to the crystallization step or back into the separation zone and be treated as previously described. Thus, a continuous process of producing highly pure L-ribose crystals is also disclosed in the present invention. The continuous process includes all of the processing steps mentioned hereinabove.

The following examples are given to illustrate the scope of the invention. Because these examples are given for illustrative purposes only the invention embodied therein should not be limited thereto.

EXAMPLE 1

In Examples 1–7 that follow, the conversion step of the present invention is exemplified.

A solution obtained by adding 40 g of L-arabinose, 400 ml of water and 2.0 g $MoO_3$ was reacted by heating at 95° C. for 3 hours under stirring. The reaction solution was cooled and analyzed by HPLC. The solution was found to contain L-arabinose (89%), L-ribose (10%). The conversion efficiency was 90%. In the present invention, the term "conversion efficiency" denotes the amount of L-ribose formed relative to the amount of L-arabinose employed in the epimerization reaction.

EXAMPLE 2

A solution obtained by adding 100 g of L-arabinose, 200 ml of water and 0.50 g $H_2MoO_4$ was reacted by heating at 95° C. for 3 hours under stirring. The reaction solution was cooled and ion exchanged to remove the catalyst. The solution was found to contain L-arabinose (71.3%), L-ribose (17.3%) and traces of xylose and lyxose. The conversion efficiency was 61%.

EXAMPLE 3

A solution obtained by adding 100 g of L-arabinose, 200 ml of water and 1.0 g $H_2MoO_4$ was reacted by heating at 95° C. for 3 hours under stirring. The reaction solution was cooled and analyzed by HPLC. The solution was found to contain L-arabinose (59.4%), L-ribose (18.6%) and xylose and lyxose. The conversion efficiency was 45.8%.

EXAMPLE 4

A solution obtained by adding 100 g of L-arabinose, 200 ml of water and 2.0 g $H_2MoO_4$ was reacted by heating at 95° C. for 3 hours under stirring. The reaction solution was cooled and analyzed by HPLC. The solution was found to contain L-arabinose (57%), L-ribose (18.9%) and xylose and lyxose. The conversion efficiency was 44.0%.

EXAMPLE 5

A solution obtained by adding 100 g of L-arabinose, 400 ml of water and 2.0 g $H_2MoO_4$ was reacted by heating at 95° C. for 3 hours under stirring. The reaction solution was cooled and analyzed by HPLC. The solution was found to contain L-arabinose (57.8%), L-ribose (22.6%) and traces of xylose and lyxose. The conversion efficiency was 53.7%.

EXAMPLE 6

A solution obtained by adding 10 g of L-arabinose, 100 ml of water and 500 ppm $MoO_3$ was reacted by heating at 95° C. for 3 hours under stirring. The reaction solution was cooled and analyzed by HPLC. The solution was found to contain L-arabinose (69.2%), L-ribose (19.1%) and traces of xylose and lyxose. The conversion efficiency was 61%.

EXAMPLE 7

A solution obtained by adding 40 g of L-arabinose, 400 ml of water and 2.0 g $(NH_4)_2MoO_4$ was reacted by heating at 95° C. for 3 hours under stirring. The reaction solution was cooled and analyzed by HPLC. The solution was found to contain L-arabinose (54.6%) and L-ribose (21.8%). The conversion efficiency was 48.1%.

EXAMPLE 8

To a water solution of L-arabinose containing 10–30 weight % L-arabinose was added 0.5–2 wt % of a Mo(IV) catalyst. The epimerization reaction took place under stirring at about 95–98° C. for about 2–3 hours with an efficiency of up to 90%. The catalyst was $MoO_3$.

About 0.5% of $MoO_3$ was added to a 10 weight % L-arabinose solution and the mixture was heated to 97° C. for 3 hours The epimerized solution contained about 20% L-ribose of the dry substance the rest being L-arabinose and traces of other sugars.

L-ribose was separated from the epimerized mixture of L-ribose and L-arabinose containing traces of other materials by chromatography on a cation exchanger in $Pb^{2+}$-form.

A chromatographic column was prepared from a polystyrene-DVB resin (i.e Finex C 16 S, 8% DVB, dp=0.34 mm). The height of the column was about 5 m. The sugar solution was allowed to flow through the column at 60° C. temperature with a speed of about 1 linear meters/hour.

From the outflow, a L-ribose rich fraction was collected for further treatment while the L-arabinose rich fraction was recirculated to the epimerization zone.

150 liters of an ion-exchanged sugar solution containing L-ribose (20%) and L-arabinose (78%) of the dry substance, was evaporated at 40° C. in vacuum to 40 weight % (Karl Fischer analysis). A column of 0.225 m diameter and 5.5 m height was filled with Finex C 13 S resin in $Pb^{2+}$-form and the sugar solution was allowed to flow through the column at atmospheric pressure. The temperature was 60° C. and the flow rate was about 1 linear meter/hour. From the outflow 115 liters of about 2 weight % L-ribose rich solution was collected. The purity of the L-ribose fraction was over 96 weight % (HPLC) analysis. The solution was subjected to cation-exchange to remove traces of Pb and other metals.

The L-ribose rich water solution containing traces of other sugars, metal salts and organic substances was purified by ion exchange chromatography and, optionally, by a second chromatographic separation.

The L-ribose rich solution was purified by ion exchange on a cation exchanger (i.e. IMAC C 16 P) in $H^+$-form to remove traces of metals. The solution was then evaporated to about 60 weight % and, optionally, subjected to a second chromatographic separation on a cation exchanger (i.e. Finex CS 11 GC, 5.5% DVB, dp=0.34 mm) in Na-form. The column height was about 5 m, the temperature was about 60° C. and the flow rate was about 1 linear meter/hour. The L-ribose rich fraction was collected for further treatment wherein the impure fraction was recycled either to the first or to the second chromatographic separation. The L-ribose rich solution was purified by cation exchange chromatography and color removal on columns containing resins in $H^+$ and $OH^+$-forms respectively (i.e. IMAC C 16 P cation exchanger and Dowex Optipore adsorbent).

A 40 weight % solution with over 96% ribose purity (HPLC) was subjected to a chromatographic separation on a cation exchange column in Na$^+$-form in order to remove impurities. The chromatographic column was 5.5 m height with a diameter of 0.225 m. The column was filled with a Finex CS 11 GC resin in Na$^+$-form. The sugar solution was allowed to flow through the column at atmospheric pressure at 60° C. temperature with a speed of 1 linear meter/hour. 30 liters of a L-ribose solution of 12 weight % and 98% purity were collected from the outflow. The ribose-fraction was subjected to cation exchange (IMAC C 16 P in H$^+$-form) and color removal (Dowex Optipore in OH$^+$-form). Both columns were about 1.5 m high with a diameter of 0.10 m.

L-ribose solution containing over 98 weight % L-ribose of the dry substance, was evaporated under vacuum at 60° C. temperature to a concentration of about 90 weight %. The temperature was then lowered to about 35–40° C. and the solution was seeded with about 1% of pulverized anhydrous crystalline L-ribose. The cooling was continued at a maximum rate of about 1° C./hour allowing the L-ribose monohydrate crystals to grow. If the viscosity of the crystal mass increased, ethanol was added to the mass at a ethanol/water ratio of 1:1–2:1. The cooling was continued to ambient temperature or below. The L-ribose crystals which amounted to about 45% of the mass was separated by centrifugation and dried in air at 20–50° C.

An analysis of the dried crystals showed that the needle form crystals are anhydrous with over 99% purity (HPLC).

EXAMPLE 9

8.63 kg chromatographically enriched and evaporated ribose syrup (DS (dry solids) 68.1% w/w, ribose 93.5%/DS) was further evaporated by a vacuum evaporator (rotating jar in 60° C. water bath). The 6.0 kg syrup (DS 92.4% w/w) was put into 6 liter vertical cooling crystallizer equipped with an agitator and a heating/cooling water jacket.

The syrup was cooled to 36° C. and seeded with dried anhydrous ribose crystals. Crystallization started vigorously after seeding. Cooling was continued only to 35° C. due to the very thick mass. Then, the mass was heated up to 40° C., diluted with 70 ml water (DS 91.6%), cooled to 25° C. and diluted again with 70 ml water (DS 90.6%). The mother liquid concentration was measured by a refractometer and some microscopic photographs were taken.

According to the analysis results and material balance calculations the crystals were monohydrate (hydrate water 10.5%) in the beginning. However, the crystal form changed to anhydrous when the mother liquid concentration was 96% w/w, supersaturation 4 and ribose yield 55%. Due to the liberation of water crystals, the mother liquid concentration dropped below 87% and the mass became less viscous. The process of crystallization according to the measurements and material balance was as follows:

| Time (hr:min) | Temp. (° C.) | DS, ml (% w/w) | Q$^1$, ml (% DS) | Yield ribose | SS$^2$ — | Remarks |
|---|---|---|---|---|---|---|
| 0 | 36.0 | 92.4 | 93.5 | 0 | 2.07 | Seeding 0.5 g |
| 1:15 | 36.0 | 92.7 | 93.0 | 7 | 2.13 | thick mass; monohydrate |
| 1:50 | 34.7 | 95.9 | 86.3 | 56 | 3.84 | Photo:very thick mass; monohydrate |
| 20:15 | 34.7 | 86.6 | 87.7 | 5i | 1.06 | Photo:white very thick mass; anhydrous |
| 45:30 | 40.0 | 88.0 | 89.2 | 43 | 1.05 | 38 000 cP; 1$^{st}$ test centrif.; anhydrous |
| 115 | 25.0 | 84.9 | 87.4 | 52 | 1.18 | 730 000 cP; 2$^{nd}$ test centrif.; anhydrous |
| 138 | 24.9 | 83.5 | 87.6 | 51 | 1.08 | 230 000 cP; 3$^{rd}$ test centrif.; anhydrous |

$^1$Q, ml denotes the ribose purity (ribose % of DS)
$^2$SS denotes the ribose supersaturation which is calculated by the following equation: SS = DS* (100-DS$^1$)/(DSL* (100-DS))

where DS=measured ribose concentration (g/100 g solution) and DS$^1$=solubility of ribose in water (g/100 g solution) at a measured temperature.

Crystal separation tests were made with a small centrifuge having a cloth on 0.15 mm screen (5500 rpm/10 min, no washing) with good mother liquid removal. Crystal and mother liquid DS and purity were analyzed.

Crystal separation was made with a large centrifuge having a 0.15 mm screen opening and a cloth (6300 rpm/5 min, no washing). 517 g crystal cake was obtained from 1078 g crystallization mass with good mother liquid removal. Separation yield was 47.9%. The analysis results of the samples are as follows:

|  | DS (% w/w) | pH — | Cond. (uS/cm) | Ribose (%/DS) |
|---|---|---|---|---|
| Crystallization mass | 93.0 | 3.7 | 60 | 93.5 |
| 1$^{st}$ test centr. cake | 94.9 | 3.9 | 38 | 96.3 |
| 2$^{nd}$ test centr. cake | 94.3 | 3.9 | 36 | 96.7 |
| 3$^{rd}$ test centr. cake | 95.0 | 4.0 | 31 | 97.0 |
| Centrif. cake | 95.2 | 3.9 | 32 | 97.1 |
| 1$^{st}$ test centr. m.1 | 87.7 | 3.6 | 72 | 89.1 |
| 2$^{nd}$ test centr. m.1 | 84.4 | 3.6 | 84 | 83.8 |
| 3$^{rd}$ test centr. m.1 | 84.1 | 3.6 | 81 | 84.5 |

DS is measured with Karl-Fisher method
pH and conductivity (cond.) are measured from 5% w/w solution at room temperature
ribose content is measured by HPLC with Pb$^{2+}$ resin

EXAMPLE 10

11.47 kg chromatographically separated and evaporated ribose syrup (DS 62.7% w/w, ribose 95%/DS) was further evaporated by a vacuum evaporator (rotating jar in 60° C. water bath). About 8 kg syrup (DS 89.4% w/w) was put into a 10 liter vertical cooling crystallizer equipped with an agitator and a heating/cooling water jacket.

The syrup was cooled to 35° C. and seeded with dried anhydrous ribose crystals. Crystallization started vigorously after seeding. The cooling was continued only to 33° C. due to the very thick mass. The mother liquid concentration was measured by refractometer and some microscopic photographs were taken. According to the analysis results and material balance calculations the crystals were monohydrate. The mother liquid concentration did not change much in spite of the very high crystallization yield (both mother liquid and crystals has some water content). Progressing of the crystallization according to the measurements and material balance are as follows:

| Time (hr:min) | Temp. (° C.) | DS, ml (% w/w) | Q, ml (% DS) | Yield ribose | SS — | Remarks |
|---|---|---|---|---|---|---|
| 0 | 35.0 | 89.4 | 95.0 | 0 | 1.50 | Seeding 0.1 g |
| 16:30 | 34.0 | 89.3 | 92.2 | 38 | 1.49 | Photo:thick mass; monohydrate |
| 35:30 | 33.0 | 87.9 | 82.5 | 75 | 4.19 | Photo:very thick; 1st test centrif., monoh. |
| 43:15 | 32.0 | 88.2 | 84.4 | 72 | 1.28 | centrifuging; monohydrate |

Crystal separation tests were made with a small centrifuge having a cloth on 0.15 mm screen (5500 rpm/10 min, no washing). 11.5 g crystal cake was obtained from 20.5 g crystallization mass with good mother liquid removal. Separation yield was 56%. Crystal and mother liquid DS and purity were analyzed.

Crystal separation was made with a large centrifuge having a 0.15 mm screen opening and cloth (6300 rpm/5 min, 80 ml 99.5% EtOH washing). Totally 255 g crystal cake was obtained from 714 g crystallization mass with good mother liquid removal. Separation yield was 35.7%. The analysis results of the samples are as follows:

|  | DS (% w/w) | pH — | Cond. (uS/cm) | Ribose (%/DS) |
|---|---|---|---|---|
| Crystallization mass | 89.2 | 4.7 | 10 | 95.0 |
| 1st test centr. cake | 92.3 | 4.7 | 8 | 96.7 |
| Centrif. cake | 94.0 | 3.9 | 40 | 97.0 |
| 2nd test centr. m.1 | 87.4 | 4.5 | 15 | 92.2 |

DS is measured with Karl-Fisher method
pH and Conductivity are measured from 5% w/w solution at room temperature
ribose content is measured by HPLC with $Pb^{2+}$ resin

EXAMPLE 11

500 g dried anhydrous ribose crystals and 50 g water were mixed in a 1000 ml vertical cooling crystallizer having a heating/cooling water jacket. Crystals were totally dissolved at 60° C.

The syrup (DS 91.0% w/w, ribose 98.6 area-%) was cooled to 40° C. and seeded with dried anhydrous ribose crystals and the cooling was continued until 35° C. The crystallization mass became very thick and it was diluted with water (DS 84.5% w/w). Cooling was then continued until 20° C. and then crystal separation was made with a large centrifuge (0.15 mm screen opening and cloth, 3000 rpm/10 min, 20 ml water washing). Totally, 85 g crystal cake was obtained from 29 g crystallization mass with good mother liquid removal. Separation yield was 28.4%.

The wet crystal cake was further purified and dried by washing with 94% EtOH. 34.6 g cake and 35 g EtOH were mixed at room temperature; then crystals were separated by centrifuging. Totally 30 g crystal cake was obtained from 70 g mass with very good mother liquid removal. Separation yield 43.0%. The analysis results of the samples are as follows:

|  | DS (% w/w) | Ribose (area-%) |
|---|---|---|
| Centrifugal mass | 84.8 | 98.6 |
| 1st centrif. cake | 90.2 | 99.3 |
| EtOH washed cake | 94.2 | 99.2 |

EXAMPLE 12

300 g dried anhydrous ribose crystals and 47 g water were mixed in a 1000 ml vertical cooling crystallizer having a heating/cooling water jacket. Crystals were totally dissolved at 55° C.

The syrup was cooled to 35° C. and seeded with dried anhydrous ribose crystals. The crystals remained in the solution. Cooling was then continued until 29.5° C. The mother liquid concentration was measured by refractometer and some microscopic photographs were taken. Ribose and DS content of the crystallization mass was analyzed 98.6 area-% and 86.4% w/w. According to the analysis results and material balance calculations the crystalline form was monohydrate. Progressing of the crystallization according to the measurements and material balance are as follows:

| Time (hr:min) | Temp. (° C.) | DS, ml (% w/w) | Q, ml (% DS) | Yield ribose | SS — | Remarks |
|---|---|---|---|---|---|---|
| 0 | 35.0 | 86.4 | 98.6 | 0 | 1.17 | Seeding 0.04 g |
| 11:00 | 33.5 | 86.3 | 95.5 | 4 | 1.21 | Photo:sparse mass |
| 38:30 | 30.5 | 86.3 | 98.5 | 4 | 1.31 | Photo sparse mass |
| 48:45 | 29.5 | 85.0 | 98.0 | 32 | 1.21 | Photo:thick mass |
| 49:50 | 29.5 | 84.7 | 97.8 | 37 | 1.17 | centrifuging |

Crystal separation was made with a small centrifuge having a 0.15 mm screen opening and a cloth (5500 rpm/10 min, no washing). Totally, 8.11 g crystal cake was obtained from 21.5 g crystallization mass with good mother liquid removal. This corresponds 33.7% separation yield and 39.4% ribose yield.

Crystal separation was made with a large centrifuge having a 0.15 mm screen opening and a cloth (3000 rpm/1 min, no washing). Totally, 155 g crystal cake was obtained from 218 g crystallization mass with poor mother liquid removal. Separation yield was 71.1%.

The wet crystal cake was further purified and dried by washing with 94% EtOH. Specifically, 90.5 g cake and 41.7 g EtOH were mixed for 30 minutes at room temperature. The crystals were then separated by centrifuging (3000 rpm/3 min, no washing). 48 g crystal cake was obtained from 123 g mass with very good mother liquid removal. Separation yield was 53.0%. The EtOH washed crystal cake was dried at room temperature for about 2 hrs. The analysis results of the samples are as follows:

|  | DS (% w/w) | pH | Ribose (area-%) |
| --- | --- | --- | --- |
| Seeding point | 86.4 | 3.2 | 98.6 |
| Test centr. cake | 89.6 | 3.7 | 99.3 |
| Test centr. m.1 | 84.4 | 3.8 | 97.9 |
| 1st centrif. cake | 87.2 | 3.4 | 99.2 |
| EtOH washed cake | 90.7 | 3.7 |  |
| Dried crystals | 91.9 | 3.6 | 99.6 |

DS is measured with Karl-Fisher method
pH is measured from 30–0% w/w solution at room temperature
ribose content is measured by HPLC with $Pb^{2+}$ resin Some dried crystals were further dried (1 hr/40° C. then 1 hr/60° C. and 16 hr in decissator over dry silica gel). The crystals were analyzed by differential scanning calorimeter with 10° C./min heating rate. There was only one endothermic peak in the thermograms: dried crystals at 91.4° C. and extra dried at 89.2° C.

The above embodiments and examples are given to illustrate the scope and spirit of the invention. These embodiments and examples will make apparent, to those skilled in the art, other embodiments and examples. These other embodiments and examples are within contemplation of the present invention; therefore, the instant invention should be limited only by the appended claims.

What is claimed is:

Having thus described our invention, what we claim as new, and desire to secure by Letters Patent is:

1. A process of preparing and recovering high purity L-ribose crystals from a solution of L-arabinose, said process comprising the steps of:

(a) heating a solution comprising L-arabinose in a stirred reaction zone and in the presence of from about 0.05 to about 5 mol %, based on the total amount of L-arabinose in said solution, of a molybdenum compound under conditions whereby 10–35% by weight of said L-arabinose is converted to L-ribose;

(b) separating said L-ribose from the heated solution of step (a) under conditions to provide at least one fraction containing L-ribose having a purity of greater than 90% of dry substance, wherein other L-sugar fractions are transferred back to said stirred reaction zone or into a chromatographic separation;

(c) crystallizing said L-ribose fraction under conditions effective to form monohydrate L-ribose crystals; and (d) recovering high purity L-ribose crystals therefrom, said high purity L-ribose crystals having a L-ribose content of greater than 95% by weight, a water content of less than 0.5% by weight and a melting point of greater than 88° C.

2. The process of claim 1 wherein said molybdenum compound is selected from the group consisting of $MoO_3$, $H_2MoO_4$, $(NH_4)_2MoO_4$ and any other salt of $MoO_4^{2-}$.

3. The process of claim 2 wherein said molybdenum compound is $MoO_3$.

4. The process of claim 1 wherein from about 0.1 to about 1 mol % of said molybdenum compound relative to said L-arabinose is employed in step (a).

5. The process of claim 4 wherein from about 0.3 to about 0.5 mol % of said molybdenum compound relative to said L-arabinose is employed in step (a).

6. The process of claim 1 wherein said heating step is carried out at a temperature of from about 60° to about 110° C. for a time period of from about 0.1 to about 24 hours.

7. The process of claim 6 wherein said heating step is carried out at a temperature of from about 92° C. to about 98° C. for a time period of from about 2 to about 3 hours.

8. The process of claim 1 wherein said L-arabinose solution comprises from about 1 to about 60% by weight L-arabinose in a solvent which is capable of dissolving said L-arabinose.

9. The process of claim 8 wherein said L-arabinose solution comprises from about 10 to about 15% by weight L-arabinose in a solvent which is capable of dissolving said L-arabinose.

10. The process of claim 8 wherein said solvent is water, an alcohol, an ether or mixtures thereof.

11. The process of claim 10 wherein said solvent is water.

12. The process of claim 1 wherein step (b) is carried out using an ion exchange resin.

13. The process of claim 12 wherein said ion exchange resin includes the use of a strong acid cation exchange resin.

14. The process of claim 13 wherein said strong acid cation exchange resin is a resin having a polystyrene/divinylbenzene skeleton.

15. The process of claim 14 wherein said resin is a $Pb^{2+}$-form resin.

16. The process of claim 15 wherein said $Pb^{2+}$-form resin comprises sulphonated polystyrene resin crosslinked with about 3 to about 16% divinylbenzene.

17. The process of claim 16 wherein said lead resin comprises sulphonated polystyrene resin crosslinked with about 8 to about 10% divinylbenzene.

18. The process of claim 1 wherein step (b) comprises transferring said heated solution formed in step (a) to a separation zone comprising a $Pb^{+2}$-form strong cation exchanger; and eluting said heated solution through said separation zone under conditions to provide said L-ribose fraction and said other L-sugar fractions.

19. The process of claim 18 wherein said heated solution is eluted through said separation zone at a flow rate of from about 0.2 to about 10 linear meters per hour and at a temperature of from about 10° to about 90° C.

20. The process of claim 19 wherein said heated solution is eluted through said separation zone at a flow rate of from about 1 to about 3 linear meters per hour and at a temperature of from about 50° to about 65° C.

21. The process of claim 1 wherein said other eluted L-sugar fractions comprise from about 20 to about 90% of dry substance L-arabinose, from about 0 to about 10% of dry substance xylose, from about 0 to about 2% of dry substance glucose, from about 0 to about 2% of dry substance galactose, from about 0 to about 5% of dry substance lyxose and from about 0 to about 5% of dry substance ribulose.

22. The process of claim 1 wherein step (c) comprises evaporating said L-ribose fraction under conditions to form a mixture having a dry solid content of from about 85% by weight or above; and cooling said mixture containing said L-ribose fraction below about 40° C. and seeding said cooled mixture with ribose crystals.

23. The process of claim 22 wherein said cooling step is conducted in water and, optionally, in the presence of at least one viscosity reducing agent.

24. The process of claim 23 wherein said viscosity reducing agent is selected from the group consisting of alcohols, hydrocarbons and water miscible organic solvents.

25. The process of claim 24 wherein said viscosity reducing agent is ethanol.

26. The process of claim 25 wherein said ethanol is added during said cooling crystallization at a temperature of below about 35° C.

27. The process of claim 22 wherein said cooling step is continued until a temperature of from about 10° to about 30° C. Is reached and is maintained at said temperature for a time period of from 0 to about 100 hours.

28. The process of claim 22 wherein, after cooling, the L-ribose crystals are purified and partially dehydrated by washing the same at least once with a dehydrating solvent.

29. The process of claim 28 wherein said dehydrating solvent is an alcohol or an anhydrous ether.

30. The process of claim 29 wherein said alcohol is ethanol.

31. The process of claim 1 wherein said recovery step includes centrifugation, washing, dehydration, filtration or a combination thereof; and drying.

32. The process of claim 31 wherein said drying step is carried out at a temperature of from about 0° to about 40° C. or a time period of from about 0.5 to about 50 hours.

33. The process of claim 32 wherein said drying step is carried out at a temperature of from about 10° to about 30° C. for a time period of from about 1 to about 10 hours.

34. The process of claim 1 wherein said purity of said separated L-ribose is greater than 95% of dry substance.

35. The process of claim 1 wherein in step (a) 15–25% by weight of said L-arabinose is converted to L-ribose.

36. The process of claim 1 wherein said L-arabinose is recovered from arabinose containing hemicellulose hydrolyzate, hardwood spent liquor or sugar beet pulp hydrolyzate.

37. The process of claim 22 wherein said dry solid content is from about 88 to about 92% by weight.

38. A process of preparing a L-ribose fraction having a purity greater than 90% of dry substance, said process comprising the steps of:
   (a) heating a solution comprising L-arabinose in a stirred reaction zone and in the presence of from about 0.05 to about 5 mol %, based on the total amount of L-arabinose in said solution, of a molybdenum compound under conditions whereby 10–35% by weight of said L-arabinose is converted to L-ribose;
   (b) transferring said reaction solution formed in step (a) to a separation zone, wherein said separation zone comprises a strong cation $Pb^{+2}$-form exchanger; and
   (c) eluting said reaction solution through said separation zone under conditions to provide at least one fraction containing L-ribose having a purity greater than 90% of dry substance, wherein other L-sugar fractions provided in said eluting step are transferred back to said stirred reaction zone or into chromatographic separation.

39. The process of claim 38 wherein said eluted fraction contains from about 97 to about 98% of dry substance L-ribose, from about 0 to about 0.5% of dry substance L-arabinose, from about 0 to about 0.5% of dry substance L-xylose, from about 0 to about 2% of dry substance L-ribulose, from about 0 to about 0.5% of dry substance L-lyxose and other minor L-sugars.

40. The process of claim 38 further comprising the steps of crystallizing said L-ribose fraction under conditions effective to form monohydrate L-ribose crystals; and recovering said L-ribose crystals from said crystallized L-ribose fraction.

41. The process of claim 40 wherein said crystallization step comprises evaporating said L-ribose fraction under conditions effective to form a mixture having a dry solid content of from about 85% by weight or above; and cooling said mixture containing said L-ribose below about 40° C. and effecting monohydrate L-ribose crystal growth at said temperature by seeding said cooled mixture with ribose crystals.

42. The process of claim 41 wherein said cooling step is conducted in water and, optionally, in the presence of at least one viscosity reducing agent.

43. The process of claim 42 wherein said viscosity reducing agent is selected from the group consisting of alcohols, hydrocarbons and water miscible organic solvents.

44. The process of claim 43 wherein said viscosity reducing agent is ethanol.

45. The process of claim 44 wherein said ethanol is added during said cooling crystallization at a temperature of below about 35° C.

46. The process of claim 41 wherein said cooling crystallization is continued to a temperature of from about 10° to about 30° C. is reached and then maintained at said temperature for a time period of from 0 to about 100 hours.

47. The process of claim 41 wherein, after cooling, the monohydrate L-ribose crystals are purified and partially dehydrated by washing the monohydrate L-ribose crystals at least once with a dehydrating solvent.

48. The process of claim 47 wherein the dehydrating solvent is an alcohol or an anhydrous ether.

49. The process of claim 48 wherein said alcohol is ethanol.

50. The process of claim 40 wherein said recovery step includes centrifugation, washing, dehydrating, filtration or a combination thereof; and drying.

51. The process of claim 41 wherein said dry solid content is from about 88 to about 92% by weight.

52. The process of claim 38 wherein 15–25% of L-arabinose by weight is converted to L-ribose.

53. A process of preparing monohydrate L-ribose crystals having a purity of greater than 99% of dry substance, said method comprising:
   (a) heating, in the absence of a metal salt, a solution comprising L-arabinose in a stirred reaction zone and, in the presence of from about 0.1 to about 1 mol %, based on the total amount of L-arabinose in said solution, of a molybdenum compound under conditions whereby 15–25% by weight of said L-arabinose is converted to L-ribose;
   (b) transferring said reaction solution formed in step (a) to a separation zone, wherein said separation zone comprises a strong cation $Pb^{+2}$-form exchanger;
   (c) eluting said reaction solution through said separation zone under conditions to provide at least one fraction containing L-ribose having a purity greater than 97% of dry substance, wherein other selected fractions provided in said eluting step are transferred back to said stirred reaction zone or into chromatographic separation;
   (d) evaporating said L-ribose fraction under conditions to form a mixture having a dry solid content of from about 85% by weight or above;
   (e) cooling said mixture containing said L-ribose below about 40° C. and effecting monohydrate L-ribose crystal growth at said temperature by seeding said cooled mixture with anhydrous ribose crystals; and
   (f) recovering said L-ribose crystals, said L-ribose crystals having a melting point of greater than 88° C.

54. The process of claim 53 wherein said dry solid content is from about 88 to about 92% by weight.

55. The method of claim 53 wherein said eluted fraction contains from about 97 to about 98% of dry substance L-ribose, from about 0 to about 0.5% of dry substance L-arabinose, from about 0 to about 0.5% of dry substance L-xylose, from about 0 to about 2% of dry substance L-ribulose, from about 0 to about 0.5% of dry substance L-lyxose and other minor L-sugars.

56. The process of claim 53 wherein prior to recovering said monohydrate L-ribose crystals are purified and partially dehydrated by washing said crystals at least once with a dehydrating solvent.

57. The process of claim 56 wherein said recrystallizing solvent is an alcohol or an anhydrous ether.

58. The process of claim 57 wherein said recrystallizing solvent is ethanol.

59. A process of crystallizing and recovering L-ribose crystals from a chromatographic separated L-ribose solution comprising the steps of:
  (a) providing a L-ribose rich aqueous solution having a L-ribose content greater than 90% of dry substance;
  (b) evaporating said L-ribose solution under conditions effective to form a mixture having a dry solid content of from about 85% by weight or above;
  (c) cooling said mixture containing said L-ribose below about 40° C. and effecting monohydrate L-ribose crystal growth at said temperature by seeding said cooled mixture with anhydrous ribose crystals; and
  (d) recovering L-ribose crystals, said high L-ribose crystals having a L-ribose content of greater than 95% by weight, a water content of less than 0.5% by weight and a melting point of greater than 88° C.

60. A process of preparing L-ribose from L-arabinose comprising the steps of (a) partial epimerization of L-arabinose to L-ribose, (b) chromatographic separation of L-ribose, and (c) crystallization of said L-ribose, said process further comprising at least two of the following steps: (i) utilization of a molybdenum compound for said partial epimerization, (ii) utilization of a $Pb^{+2}$-form cation exchange resin for said chromatographic separation; or (iii) utilization of crystallizing conditions in said crystallization step that are effective to form L-ribose monohydrate crystals.

61. A product comprising crystalline L-ribose having a L-ribose content of greater than 95% by weight, a water content of less than 0.5% by weight and a melting point of greater than 88° C.

62. The product of claim 61 wherein said crystalline L-ribose has a particle size of about 50 to about 100 micrometers.

63. The product of claim 61 wherein said crystalline L-ribose has an optical purity of greater than 99%.

64. The process of claim 53 wherein said molybdenum compound is selected from the group consisting of $MoO_3$, $H_2MOO_4$, $(NH_4)_2MoO_4$ and any other salt of $MoO^{2-}_4$.

65. The process of claim 64 wherein said molybdenum compound is $MoO_3$.

66. The process of claim 60 wherein said molybdenum compound is selected from the group consisting of $MoO_3$, $H_2MOO_4$, $(NH_4)_2MoO_4$ and any other salt of $MoO^{2-}_4$.

67. The process of claim 66 wherein said molybdenum compound is $MoO_3$.

* * * * *

UNITED STATES PATENT AND TRADEMARK OFFICE
CERTIFICATE OF CORRECTION

PATENT NO. : 6,140,498
DATED : October 31, 2000
INVENTOR(S) : J. Jumppanen et al.

It is certified that error appears in the above-identified patent and that said Letters Patent is hereby corrected as shown below:

<u>Title page,</u>
Item [56], References Cited, OTHER PUBLICATION, "Japanese Abstract," reference, "Jul. 10, 1980" should read -- Jun. 10, 1980 --

<u>Column 12,</u>
Line 6, "5i" should read -- 51 --

<u>Column 13,</u>
Line 6, "4.19" should read -- 1.19 --

<u>Column 14,</u>
Line 37, "95.5" should read -- 98.5 --

<u>Column 17,</u>
Line 3, "30°C. Is" should read -- 30° C is --

<u>Column 20,</u>
Lines 22 and 27, "MOO3" should read -- MoO3 --

Signed and Sealed this

Twenty-eighth Day of June, 2005

JON W. DUDAS
*Director of the United States Patent and Trademark Office*